United States Patent [19]

Johnson

[11] Patent Number: 5,073,188

[45] Date of Patent: Dec. 17, 1991

[54] HERBICIDAL AMIDES OF 4-TRIFLUOROMETHYL-3'-CARBOXYL-4'-NITRODIPHENYL ETHERS

[75] Inventor: Wayne O. Johnson, Warminster, Pa.

[73] Assignee: Rohm and Haas Company, Philadelpha, Pa.

[21] Appl. No.: 96,217

[22] Filed: Sep. 8, 1987

Related U.S. Application Data

[60] Continuation of Ser. No. 626,598, Jul. 5, 1984, abandoned, which is a continuation of Ser. No. 315,098, Oct. 21, 1981, abandoned, which is a division of Ser. No. 907,636, May 19, 1978, abandoned.

[51] Int. Cl.$^5$ .................. A01N 33/02; A01N 33/16; C07C 255/50; C07D 279/04; C07D 211/06; C07D 279/06
[52] U.S. Cl. .......................... 71/92; 71/88; 71/98; 71/105; 540/607; 546/226; 548/200; 548/214; 548/215; 548/240; 548/300; 548/356; 548/539; 558/415; 544/3; 544/53; 544/59; 544/63; 544/88; 544/163; 544/238; 544/335; 544/391
[58] Field of Search ............... 558/415; 548/200, 214, 548/215, 240, 300, 356, 539; 546/226; 544/3, 53, 59, 63, 88, 163, 238, 335, 391; 540/607; 71/88, 92, 98, 105

[56] References Cited

U.S. PATENT DOCUMENTS

| | | | |
|---|---|---|---|
| 3,798,276 | 3/1974 | Barger | 558/415 |
| 4,209,318 | 6/1980 | Johnson | 558/415 |

FOREIGN PATENT DOCUMENTS

| | | | |
|---|---|---|---|
| 49-62635 | 6/1974 | Japan | 558/415 |
| 49-62637 | 6/1974 | Japan | 558/415 |
| 49-66828 | 6/1974 | Japan | 558/415 |

*Primary Examiner*—Johann Richter
*Attorney, Agent, or Firm*—Polly E. Ramstad

[57] ABSTRACT

Compounds of the formula

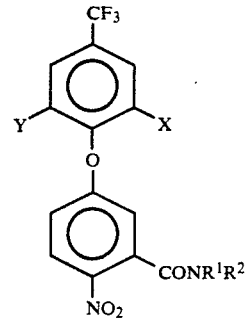

wherein
 x is a hydrogen atom, a halogen atom, a trihalomethyl group, an alkyl group, or a cyano group,
 Y is a hydrogen atom or a halogen atom,
 $R^1$ is a hydrogen atom, a hydroxy group, an alkoxy group, or an optionally-substituted alkyl group, and
 $R^2$ is a hydrogen atom or an optionally-substituted alkyl group, or $R^1$ and $R^2$ can be taken together to form a heterocyclic ring, and compositions containing these compounds exhibit herbicidal activity.

13 Claims, No Drawings

HERBICIDAL AMIDES OF 4-TRIFLUOROMETHYL-3'-CARBOXYL-4'-NITRODIPHENYL ETHERS

This application is a continuation of application Ser. No. 626,598, filed July 5, 1984, now abandoned, which is a continuation of application Ser. No. 315,098, filed Oct. 21, 1981, now abandoned, which is a divisional of application Ser. No. 907,636 filed May 19, 1978, now abandoned.

THE DISCLOSURE

This invention relates to novel compounds which show activity as herbicides, to novel herbicidal compositions which contain these compounds, and to new methods of controlling weeds with these herbicidal compositions.

In accordance with the present invention, there is provided a new class of novel diphenyl ethers having the formula

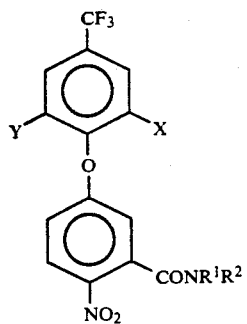

(I)

wherein
X is a hydrogen atom, a halogen atom, preferably a fluorine atom or a chlorine atom, a trihalomethyl group, preferably a trifluoromethyl group, an alkyl group, preferably having 1 to 4 carbon atoms, most preferably a methyl group, or a cyano group,
Y is a hydrogen atom or a halogen atom, preferably a fluorine atom or a chlorine atom,
$R^1$ is a hydrogen atom, a hydroxy group, a $(C_1-C_4)$ alkoxy group, an alkyl group, preferably having 1 to 4 carbon atoms, optionally substituted with one or more halogen atoms, hydroxy groups, $(C_1-C_4)$ alkoxy groups, cyano groups, thiol groups, $(C_1-C_4)$ alkylthio groups, carboxy groups, or agronomically-acceptable salts thereof, or carb($C_1-C_4$)alkoxy groups, or a cycloalkyl group, preferably having one carbocyclic ring and 5 to 7 carbon atoms, and
$R^2$ is a hydrogen atom, an alkyl group, preferably having 1 to 4 carbon atoms, optionally substituted with one or more halogen atoms, hydroxy groups, $(C_1-C_4)$ alkoxy groups, cyano groups, thiol groups, $(C_1-C_4)$ alkylthio groups, carboxy groups, or agronomically-acceptable salts thereof, or carb(-$C_1-C_4$)alkoxy groups, or a cycloalkyl group, preferably having one carbocyclic ring and 5 to 7 carbon atoms, or
$R^1$ and $R^2$ can be taken together with the attached nitrogen atom to form a saturated heterocyclic ring having 4 to 6 carbon atoms and up to one additional hetero nitrogen, oxygen, or sulfur atom.

When the X, $R^1$, or $R^2$ substituent is an alkyl group, it can have either a straight- or branched-chain configuration. When $R^1$ or $R^2$ is a substituted alkyl group, it will preferably have a single substituent.

These novel compounds have been found to show unexpected activity as weed control agents. In a preferred embodiment of the invention, X is a halogen atom, most preferably a chlorine atom, Y is a hydrogen atom and $R^1$ and $R^2$ are individually a hydrogen atom or a substituted or unsubstituted $(C_1-C_4)$alkyl group, more preferably a hydrogen atom or an unsubstituted $(C_1-C_4)$ alkyl group. Most preferably either $R^1$ or $R^2$ is a hydrogen atom, and the other an unsubstituted $(C_1-C_4)$ alkyl group.

Examples of the compounds of the invention embraced by Formula I include:
2-Nitro-5-(2-chloro-4-trifluoromethylphenoxy)-N-methylbenzamide
2-Nitro-5-(2-chloro-4-trifluoromethylphenoxy)-N,N-diethylbenzamide
2-Nitro-5-(2-chloro-4-trifluoromethylphenoxy)-N-t-butylbenzamide
2-Nitro-5-(2-bromo-4-trifluoromethylphenoxy)-N-(2-hydroxyethyl)benzamide
2-Nitro-5-(2-fluoro-4-trifluoromethylphenoxy)-N,N-4-oxapentamethylenebenzamide
2-Nitro-5-(2,6-dichloro-4-trifluoromethylphenoxy)-N-methyl-N-(2-hydroxypropyl)benzamide
2-Nitro-5-(2-chloro-4-trifluoromethylphenoxy)-N-cyclohexylbenzamide
2-Nitro-5-(2-cyano-4-trifluoromethylphenoxy)-N-carboxymethylbenzamide
2-Nitro-5-(2,4-bistrifluoromethylphenoxy)-N-ethyl-N-(methylthioethyl)benzamide
2-Nitro-5-(2-chloro-4-trifluoromethylphenoxy)-N-(2-ethoxyethyl)benzamide
2-Nitro-5-(2-chloro-4-trifluoromethylphenoxy)-N-ethylbenzamide
2-Nitro-5-(2-fluoro-4-trifluoromethylphenoxy)-N-methyl-N-(1-carbethoxy)ethylbenzamide
2-Nitro-5-(2-chloro-6-fluoro-4-trifluoromethylphenoxy)-N-methylbenzamide
2-Nitro-5-(4-trifluoromethylphenoxy)-N,N-pentamethylenebenzamide
2-Nitro-5-(2-chloro-4-trifluoromethylphenoxy)-N-carboxymethyl-N-(2-hydroxyethyl)benzamide
2-Nitro-5-(2-cyano-4-trifluoromethylphenoxy)benzamide
2-Nitro-5-(4-trifluoromethylphenoxy)-N-(2-cyanoethyl)benzamide
2-Nitro-5-(2-chloro-4-trifluoromethylphenoxy)-N,N'-bis-(2-hydroxyethyl)benzamide
2-Nitro-5-(2-fluoro-4-trifluoromethylphenoxy)-N-hydroxybenzamide
2-Nitro-5-(2,6-dichloro-4-trifluoromethylphenoxy)-N-methoxybenzamide The novel diphenyl ethers of the invention are useful both as preemergence and postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the plants have emerged and during their growth period. Compounds of the invention are particularly active against broadleaf weeds.

Among the crops on which the diphenyl ethers of the invention can be advantageously employed are, for example, soybeans, peanuts, cotton, corn, wheat, barley, rice and other cereal crops, and the like.

When used in transplanted rice crops, the ethers can be applied either preemergence or postemergence to the weeds--that is, they can be applied to the growth medium of the transplanted plants either before the weed plants have emerged or while they are in their early stages of growth. The ethers can be applied to the growth medium either before or after the rice has been transplanted to that medium.

The diphenyl ethers of the invention can be applied in any amount which will give the desired degree of weed control. A preferred rate of application of the herbicides of the invention is from about 0.1 to 12, and most preferably about 0.25 to 4, pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

A diphenyl ether of the invention can be applied to the growth medium or to plants to be treated either by itself or, as is generally done, as a component in a herbicidal composition or formulation which also comprises an agronomically acceptable carrier. By agronomically-acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The diphenyl ether compounds of this invention can be formulated in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentratation of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as a granular fuller's earth, vermiculite, ground corn cobs, seed hulls, including bran or other grainhulls, or similar material. A solution of one or more of the diphenyl ethers in a volatile organic solvent is then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing compostion in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the methods of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts

Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate

Phenols dinitro-o-(sec-butyl)phenol and its salts
pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea

Substituted Triazines 2-chloro-4,6-bis(ethylamino)-s-triazine
2-chloro-4-ethylamino-6-isopropylamino)-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropyoamino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-ethoxy-4'-nitrodiphenyl ether
2-chloro-4-trifluoromethyl-4'-nitrodiphenyl ether
2-chloro-4-trifluoromethyl-3'-carbethoxy-4'-nitrodiphenyl ether
2,4-dichloro-3'-carbomethoxy-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide
N-isopropyl-N-phenylchloroacetamide
N-n-butoxymethyl-N-(2,6-diethylphenyl)chloroacetamide
N-n-methoxymethyl-N-(2,6-diethylphenyl)chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid 2,3-dichloro-1,4-naphthoquinone di(methoxythiocarbonyl)disulfide
3-isopropyl-1H-2,1,3-benzothiazidzin-(4)3H-one-2,2-dioxide
6,7-dihydrodipyrido[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.
4-Amino-6-(1,1-dimethylethyl)-3-methylthio-1,2,4-triazin-5-(4H)-one
3-Amino-2,5-dichlorobenzoic acid
$N^3,N^3$-Diethyl-2,4-dinitro-6-trifluoromethyl-1,3-phenylene-diamine
N-(2-chloroethyl)-2,6-dinitro-N-propyl-4-trifluoromethylaniline
N-Cyclopropylmethyl-α,α,α-trifluoro-2,6-dinitro-N-propyl-p-toluidine
N-(1-Ethylpropyl)-3,4-dimethyl-2,6-dinitrobenzeneamine
S-(O,O-diisopropyl)phosphorodithioate ester of N-(2-mercaptoethyl)benzenesulfonamide
2-(α-Napthoxy)-N,N-diethylpropionamide
2-Chloro-N-(2-ethyl-6-methylphenyl)-N-(2-methoxy-1-methylethyl)acetamide
Methylsulfanilylcarbamate
3-(p-(p-Chlorophenoxy)phenyl)-1,1-dimethylurea
Phosphonomethylglycine
Methyl 2-(4-(2,4-dichlorophenoxy)phenoxy)propionate
Sodium 2- 4-[(3,5-dichloro)-2-pyridyloxy]phenoxy propionate
Methyl 2-(4-(4-trifluoromethylphenoxy)phenoxy)propionate When mixtures of herbicides are employed, the relative proportions which are used will depend upon the crop to be treated and the degree of selectivity in weed control which is desired, The ethers of the invention can be prepared by reacting an acid halide, preferably an acid chloride of a diphenyl ether of the formula

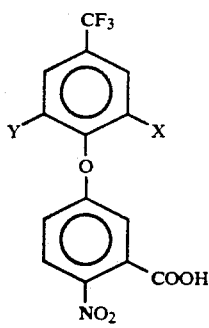

(II)

wherein X and Y are as defined above, with an excess of an amine of the formula

HNR$^1$R (III)

wherein R$^1$ and R$^2$ are as defined above. This reaction is generally carried out in a solvent in which the acid chloride is soluble, such as diethyl ether, a chlorinated hydrocarbon, an aromatic hydrocarbon, or the like, at a temperature of about 0° to about 100° C., preferably at about 0° to about 40° C. The amination reaction can also be carried out under Schotten-Bauman conditions, where one equivalent of an amine of Formula III is first added to a mixture of an organic solvent, such as diethyl ether or the like, and an aqueous solution of a strong inorganic base, such as sodium hydroxide, or the like, followed by the slow addition of an organic solution of the acid chloride, for example in toluene, to the agitated two-phase system. This reaction is generally carried out at a temperature of about 0° to about 100° C., preferably about 10° to about 40° C.

Compounds of the invention can also be prepared by reacting an ester of a diphenyl ether of Formula II with an amine of Formula III, using an acid catalyst, such as p-toluenesulfonic acid, hydrochloric acid, sulfuric acid or the like in a suitable inert solvent, such as tetrahydrofuran, glyme, toluene, xylene, or the like, at a temperature of about 20° to the reflux temperature of the solvent. In another route to the compounds of the invention, an ammonium salt of a diphenyl ether of Formula II, in which the cation has the formula $\oplus NH_2R^1R^2$ (IIIa)

wherein R$^1$ and R$^2$ are as defined above, is heated at a temperature of about 100° to about 200° in a high-boiling inert solvent, such as toluene, xylene, diglyme, or the like, to produce the amide directly.

The diphenyl ether precursors can be prepared by reacting a suitably substituted phenol, or the potassium or sodium salt of the phenol, with a suitably substituted halobenzene, such as a chloro- or fluorobenzene in the presence of an alkaline agent. Such precursors and their preparation are described in U.S. Pat. No. 3,928,416, of Bayer et al., granted Dec. 23, 1975, and U.S. Pat. No. 4,031,131, of Johnson, granted June 21, 1977, which are incorporated herein by reference.

Another route to the compounds of the invention involves the nitration of a diphenyl ether of the formula

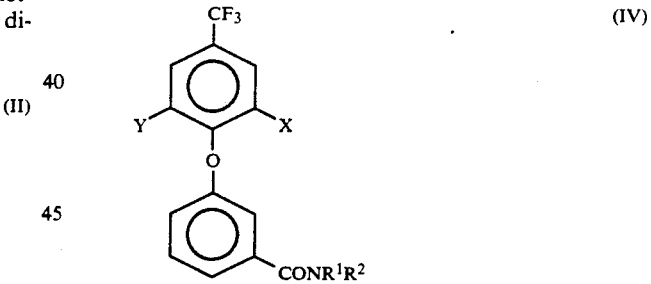

(IV)

wherein X, Y, R$^1$ and R$^2$ are as defined above, using typical nitrating agents such as potassium nitrate in sulfuric acid, acetyl nitrate, mixed sulfuric acid/nitric acid, nitrosonium tetrafluoroborate, and the like. The nitration reaction is generally carried out at about 20° to about 100° C., preferably about 0° to about 5° C., optionally in the presence of an inert organic solvent, such as methylene chloride or other chlorinated hydrocarbon.

Amides of the invention can also be prepared by condensing a phenol of the formula

(V)

wherein X and Y are as defined above with a substituted halobenzene of the formula chloro-4-trifluoromethylphenoxy)benzoyl chloride (8 g.) m.p. 118°–120° C.

TABLE I

Diphenyl Ethers - Physical Data

| Example No. | R¹ | R² | m.p. (°C.) | | % C | % H | % N | % Cl | % F |
|---|---|---|---|---|---|---|---|---|---|
| 1 | H | H | m.p. 139–143 | Found | 45.77 | 2.30 | 7.91 | | |
| | | | | reqs | 46.62 | 2.23 | 7.76 | | |
| 2 | Me | H | m.p. 118–120 | Found | 47.41 | 2.87 | 6.96 | 9.32 | 14.45 |
| | | | | reqs | 48.08 | 2.69 | 7.49 | 9.46 | 15.21 |
| 3 | Et | H | m.p. 120–122 | Found | 49.49 | 3.14 | 7.02 | 9.17 | 14.51 |
| | | | | reqs | 49.44 | 3.11 | 7.21 | 9.12 | 14.66 |
| 4 | Me | Me | oil | Found | 48.13 | 3.49 | 6.87 | 11.64 | 14.75 |
| | | | | reqs | 49.44 | 3.11 | 7.21 | 9.12 | 14.66 |
| 5 | Et | Et | m.p. 75–90 | Found | 50.26 | 3.84 | 6.04 | 9.94 | 13.90 |
| | | | | reqs | 51.80 | 3.88 | 6.73 | 8.55 | 13.68 |
| 6 | i-Pr | H | m.p. 135–137 | Found | 55.19 | 4.47 | 7.49 | 9.24 | 15.07 |
| | | | | reqs | 54.77 | 4.32 | 7.51 | 9.51 | 15.28 |

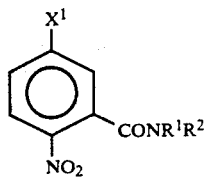

(VI)

wherein $X^1$ is a halogen atom, preferably a fluorine atom, and $R^1$ and $R^2$ are as defined above. This reaction is generally carried out at a temperature of about 0° to about 250° C., preferably about 75° to about 200° C., optionally in the presence of an appropriate solvent, such as sulfolane, dimethylsulfoxide, dimethylformamide, hexamethylphosphorustriamide, or other inert polar organic solvent.

The following examples will further illustrate this invention but are not intended to limit it in any way. In Table I, typical diphenyl ethers of the invention are listed with their elemental analyses. A specific illustrative preparation of the compound of Example 2 is set forth before Table I. All temperatures are in degrees Celsius and parts and percentages are by weight unless otherwise indicated.

EXAMPLE 2

Experimental

Preparation of 2-nitro-5-(2-chloro-4-trifluoromethylphenoxy-N-methylbenzamide

A solution of 2-nitro-5-(2-chloro-4-trifluoromethylphenoxy)benzoyl chloride (10 g., 0.026 mole) and an excess of methylamine was stirred at room temperature in toluene for five hours. Amine hydrochloride was filtered off and the filtrate stripped to yield 2-(nitro-5-(2-

The following examples show the herbicidal properties of diphenyl ethers of the invention.

EXAMPLE 6

This example shows the herbicidal activity of diphenyl ethers of the invention towards a number of common weeds. Using the procedure described below, diphenyl ethers are evaluated for control of various plant species.

The following test procedure is employed. Seeds of selected crops and weeds are planted in soil in trays. For preemergence tests, the trays are treated with the test compound immediately after the planting. For postemergence tests, the seeds are allowed to germinate, and after two weeks the trays are treated with the test compound immediately after the planting. The compound to be evaluated is dissolved in acetone, diluted with water, and sprayed over the trays using a carrier volume equivalent to 50 gallons per acre at the rate of application of two or four pounds per acre. About two weeks after the application of the test compound, the state of growth of the plants is observed and the phytotoxic effect of the compound is evaluated. The results of typical tests are summarized in Table II, which gives the average percent control achieved by the test compounds with 0 representing no weed control and 100 complete kill of the plant.

The following species were tested:

| Monocots | |
|---|---|
| barnyardgrass | Echinochloa crusgalli |
| downybrome | Bromus tectorum |
| green foxtail | Setaria vividis |
| johnsongrass | Sorghum halepense |
| yellow nutsedge | Cyperus esculentus |
| wild oats | Avena fatua |
| Dicots | |
| cocklebur | Xanthium pensylvanicum |

| | |
|---|---|
| marigold | *Tagetes patula* |
| tomato | *Lycopersicum esculentum* |
| morningglory | *Ipomoea sp* |
| nightshade | *Solanum nigrum* |
| velvetleaf | *Abutilon theophrasti* |
| safflower | *Carthamus tinctorius* |

TABLE II

Greenhouse Weed Control Data

| Compound of Example No. | | lb/A | Monocot | | | | | |
|---|---|---|---|---|---|---|---|---|
| | | | Barnyardgrass | Downybrome | Green foxtail | Johnsongrass (seedlings) | Yellow nutsedge | Wild oats |
| 1 | Pre | 2 | 99 | 60 | 100 | 100 | 99 | 30 |
| | Post | 2 | 70 | 50 | 70 | 90 | 40 | 40 |
| 2 | Pre | 2 | 99 | 40 | 100 | 99 | 100 | 95 |
| | Pre | 4 | 100 | 95 | 100 | 100 | 100 | 95 |
| | Post | 2 | 90 | 30 | 100 | 70 | 100 | 30 |
| | Post | 4 | 90 | 20 | 95 | 30 | 50 | 40 |
| 3 | Pre | 2 | 99 | 20 | 100 | 99 | 80 | 99 |
| | Pre | 4 | 100 | 40 | 100 | 99 | 99 | 95 |
| | Post | 2 | 70 | 20 | 99 | 40 | 60 | 20 |
| | Post | 4 | 80 | 70 | 100 | 60 | 99 | 50 |
| 4 | Pre | 2 | 95 | 50 | 99 | 50 | 20 | 30 |
| | Pre | 4 | 99 | 70 | 100 | 90 | 95 | 95 |
| | Post | 2 | 40 | 0 | 80 | 30 | 80 | 20 |
| | Post | 4 | 50 | 20 | 95 | 20 | 60 | 20 |
| 5 | Pre | 4 | 40 | 0 | 80 | 50 | 0 | 0 |
| | Post | 4 | 0 | 0 | 0 | 0 | 0 | 0 |

| Compound of Example No. | | lb/A | Dicot | | | | | | |
|---|---|---|---|---|---|---|---|---|---|
| | | | Cocklebur | Marigold | Tomato | Morningglory | Nightshade | Velvetleaf | Safflower |
| 1 | Pre | 2 | 70 | — | — | 70 | 100 | 60 | 0 |
| | Post | 2 | 100 | — | — | 95 | 100 | 100 | 80 |
| 2 | Pre | 2 | 80 | 100 | 100 | 90 | — | 99 | — |
| | Pre | 4 | 80 | 100 | 100 | 80 | — | 95 | — |
| | Post | 2 | 70 | 99 | 95 | 60 | — | 100 | — |
| | Post | 4 | 70 | 70 | 40 | 70 | — | 95 | — |
| 3 | Pre | 2 | 0 | 100 | 100 | 80 | — | 100 | — |
| | Pre | 4 | 60 | 100 | 100 | 95 | — | 100 | — |
| | Post | 2 | 60 | 95 | 90 | 80 | — | 90 | — |
| | Post | 4 | 60 | 95 | 60 | 60 | — | 80 | — |
| 4 | Pre | 2 | 0 | 100 | 70 | 10 | — | 80 | — |
| | Pre | 4 | 0 | 100 | 100 | 40 | — | 100 | — |
| | Post | 2 | 90 | 99 | 100 | 90 | — | 100 | — |
| | Post | 4 | 80 | 99 | 90 | 60 | — | 100 | — |
| 5 | Pre | 4 | 0 | — | — | 0 | 0 | 0 | 0 |
| | Post | 4 | 40 | — | — | 10 | 30 | 30 | 30 |

— indicates not tested

EXAMPLE 7

This example shows the selectivity of the diphenyl ethers of the invention towards several common crops, including corn, cotton, rice, soybeans and wheat. Using a procedure similar to Example 6, the following crops were planted and treated—corn, cotton, rape, rice, sugarbeet, soybeans and wheat. The results of typical tests are summarized in Table III, which gives the average percent injury caused by the test compound with 0 representing no injury and 100 complete kill of the plant.

TABLE III

| Compound of Example No. | | lb/A | Preemergence | | | | | | | Postemergence | | | | | | |
|---|---|---|---|---|---|---|---|---|---|---|---|---|---|---|---|---|
| | | | CN | COT | RA | RI | SB | SOY | WHT | CN | COT | RA | RI | SB | SOY | WHT |
| 1 | NHMe | 2 | 80 | 0 | 100 | 30 | 100 | 50 | 15 | 5 | 80 | 80 | 20 | 80 | 40 | 5 |
| | | 1 | 15 | 0 | 100 | 20 | 100 | 20 | 10 | 5 | 60 | 90 | 10 | 80 | 20 | 10 |
| | | ½ | 20 | 0 | 100 | 15 | 100 | 0 | 10 | 5 | 60 | 80 | 20 | 80 | 20 | 5 |
| 2 | NHEt | 2 | 30 | 0 | 100 | 10 | 90 | 0 | 20 | 5 | 30 | 80 | 15 | 50 | 20 | 5 |
| | | 1 | 10 | 0 | 100 | 20 | 100 | 0 | 10 | 0 | 30 | 80 | 15 | 50 | 10 | 0 |
| | | ½ | 0 | 0 | 100 | 10 | 95 | 0 | 10 | 0 | 40 | 70 | 10 | 45 | 10 | 5 |
| 4 | NMe$_2$ | 2 | 0 | 0 | 100 | 10 | 95 | 0 | 10 | 5 | 35 | 70 | 10 | 65 | 10 | 5 |
| | | 1 | 10 | 0 | 100 | 10 | 90 | 0 | 0 | 0 | 25 | 70 | 5 | 70 | 10 | 5 |
| | | ½ | 10 | 0 | 95 | 10 | 70 | 0 | 0 | 0 | 25 | 70 | 5 | 50 | 15 | 5 |
| 5 | NEt$_2$ | 2 | 0 | 0 | 100 | 0 | 100 | 0 | 5 | 15 | 30 | 80 | 5 | 60 | 10 | 10 |
| | | 1 | 0 | 0 | 95 | 0 | 95 | 0 | 5 | 15 | 30 | 80 | 5 | 50 | 15 | 15 |
| | | ½ | 0 | 0 | 80 | 0 | 90 | 0 | 10 | 20 | 20 | 70 | 0 | 55 | 10 | 5 |

It is to be understood that changes and variations can be made without departing from the spirit and scope of this invention as defined by the appended claims.

I claim:

1. A compound of the formula

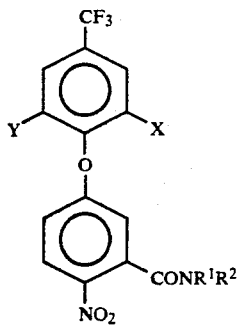

wherein
X is a cyano group,
Y is a hydrogen atom or a halogen atom,
$R^1$ is a hydroxy group or a $(C_1-C_4)$alkoxy group, and
$R^2$ is a $(C_1-C_4)$alkyl group optionally substituted with a halogen atom, a hydroxy group, a $(C_1-C_4)$alkoxy group, a cyano group, a thiol group, a $(C_1-C_4)$alkylthio group, a carboxy group, or an agronomically-acceptable salt thereof, or a carb$(C_1-C_4)$alkoxy group, or a monocyclic $(C_5-C_7)$cycloalkyl group, or
$R^1$ and $R^2$ can be taken together with the attached nitrogen atom to form saturated heterocyclic ring selected from N,N-pentamethylene and N,N-4-oxapentamethylene.

2. A herbicidal composition which comprises a compound of claim 1 and an agronomically-acceptable carrier.

3. The composition of claim 2 which additionally comprises a surfactant.

4. A method of controlling weeds which comprises applying to the surface of the growth medium prior to the emergence of the weeds from the growth medium a compound of claim 1 in an amount effective to control the growth of the weeds.

5. The method of claim 4 wherein the compound is applied in an amount of from about 0.1 to about 12 pounds per acre.

6. A method of controlling weeds which comprises applying to weed seedlings a compound of claim 1 in an amount sufficient to control the growth of the seedlings.

7. The method of claim 6 wherein the compound is applied in an amount of about 0.1 to about 12 pounds per acre.

8. A method for selectively controlling weeds in an agronomic crop which comprises applying to the area in which the crop is growing or is to be grown a compound of claim 1 in an amount sufficient to control the growth of the weeds without significantly affecting the growth of the agronomic crop.

9. The method of claim 8 wherein the crop is corn, cotton, rice, soybeans, or wheat.

10. A compound of the formula

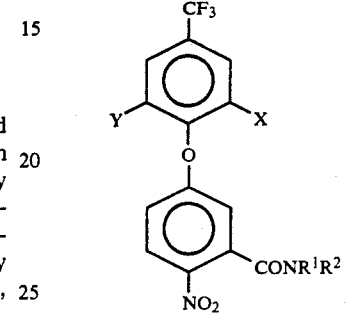

wherein
X is a cyano group,
Y is a hydrogen atom or a halogen atom,
$R^1$ is a hydroxy group or a $(C_1-C_4)$alkoxy group, and
$R^2$ is a $(C_1-C_4)$alkyl group substituted with a halogen atom, a cyano group, a thiol group, a $(C_1-C_4)$alkylthio group, a carboxy group or an agronomically acceptable salt thereof, or a carb$(C_1-C_4)$alkoxy group, or a monocyclic $(C_5-C_7)$cycloalkyl group.

11. A herbicidal composition which comprises a compound of claim 10 and an agronomically acceptable carrier.

12. The composition of claim 2 which additionally comprises a surfactant.

13. A method of controlling weeds which comprises applying to the growth medium of weeds the compound of claim 10 in an amount effective to control the growth of the weeds.

* * * * *

UNITED STATES PATENT AND TRADEMARK OFFICE
CERTIFICATE OF CORRECTION

PATENT NO. : 5,073,188
DATED : December 17, 1991
INVENTOR(S) : Wayne O. Johnson

It is certified that error appears in the above-identified patent and that said Letters Patent is hereby corrected as shown below:

In Claim 12, line 1, change "2" to --11--.

Signed and Sealed this

Eighth Day of June, 1993

Attest:

MICHAEL K. KIRK

*Attesting Officer*  Acting Commissioner of Patents and Trademarks